United States Patent

Gruber et al.

[11] Patent Number: 5,364,646
[45] Date of Patent: Nov. 15, 1994

[54] ORAL PHARMACEUTICAL FORMS OF PIMOBENDAN

[75] Inventors: Peter Gruber, Bottmingen; Willy Roth; Gottfried Schepky, both of Biberach, all of Germany

[73] Assignee: Dr. Karl Thomae GmbH, Biberach an der Riss, Germany

[21] Appl. No.: 33,659

[22] Filed: Mar. 16, 1993

Related U.S. Application Data

[63] Continuation of Ser. No. 907,003, Jul. 1, 1992, abandoned, which is a continuation of Ser. No. 644,161, Jan. 22, 1991, abandoned.

[30] Foreign Application Priority Data

Jan. 10, 1990 [DE] Germany .................. 4001622

[51] Int. Cl.$^5$ ............... A61K 9/20; A61K 9/48
[52] U.S. Cl. ................... 424/464; 424/452; 424/465; 424/468; 424/480; 424/489; 424/456; 514/960; 514/962

[58] Field of Search ......... 424/464, 468, 486, 489, 424/452, 465, 456; 514/960, 962

[56] References Cited

U.S. PATENT DOCUMENTS

| | | | |
|---|---|---|---|
| 4,361,563 | 11/1982 | Austel et al. | 514/247 |
| 4,427,648 | 1/1984 | Brickl et al. | 424/459 |
| 4,596,705 | 6/1986 | Schepky et al. | 424/468 |
| 4,704,284 | 11/1987 | Beatty et al. | 424/469 |
| 4,732,915 | 3/1988 | Ayer et al. | 424/468 X |
| 4,973,469 | 11/1990 | Mulligan et al. | 424/486 X |

*Primary Examiner*—Thurman K. Page
*Assistant Examiner*—Robert H. Harrison
*Attorney, Agent, or Firm*—D. E. Frankhouser; A. R. Stempel; M. E. M. Timbers

[57] ABSTRACT

Pharmaceutical forms of pimobendan for oral administration comprising citric acid, whereby a constant, satisfactory resorption is ensured even when there are major pH fluctuations in the gastrointestinal tract.

9 Claims, 5 Drawing Sheets

Plasma level of pimobendan 5 mg p.o., tablet without citric acid, dog, n=5, MV ± S.D. (Example 1a).

Plasma level of pimobendan 5 mg p.o., tablet without citric acid, dog, n= 5, M V ± S.D. (Example 1a).

Plasma level of pimobendan 5 mg p.o., tablet containing 50 mg citric acid, dog, n=5, MV ± S.D. (Example 1b).

UD-CG 115 BS plasma level after the administration of 5 mg pimobendan (Test subjects).

Average plasma level pattern of pimobendan on the same 4 test subjects after oral administration of a 2·5 mg tablet (■) and a capsule (●) (MV±S.D.).

ORAL PHARMACEUTICAL FORMS OF PIMOBENDAN

This is a continuation of application Ser. No. 07/907,003, filed Jul. 1, 1992, now abandoned, which is a continuation of application Ser. No. 07/644,161, filed Jan. 22, 1991, now abandoned.

The invention relates to pharmaceutical forms of pimobendan for oral administration. Pimobendan is 4,5dihydro-6-[2-(4-methoxyphenyl)-1H-benzimidazol-5-yl]-5-methyl-3(2H)-pyridazinone which was described in European Patent No. 8391; pimobendan is a substance having cardiotonic, hypotensive and anti-thrombotic activities.

Unlike other substances having different structures mentioned in this patent specification, the resorption of pimobendan when administered orally is prone to considerable inter- and intra-individual fluctuations if the active substance is incorporated in known or conventional pharmaceutical forms for oral administration. The reason for this is that pimobendan is characterized by a low solubility in aqueous media and a very highly pH-dependent solubility.

Depending on the buffer system used, about 100 to 300 mg/l dissolve at a pH between 1 and 3 (corresponding to a 0.01 to 0.03% solution), but at pH 5 only about 1 mg/l will dissolve in water (corresponding to a 0.0001% solution or 1 ppm).

In in vivo tests on humans with pimobendan packed into hard gelatin capsules, one test subject showed no blood level of pimobendan, a second test subject showed a very low blood level and a third showed higher blood levels, but overall the blood levels of pimobendan fluctuated very considerably from one individual to another and the levels were too low. These unsatisfactory resorption characteristics can be explained primarily by the high pH-dependency of the solubility of pimobendan in aqueous media and by fluctuating pH conditions in the gastrointestinal tracts of the test subjects. It is known that the pH of the gastric juices, particularly in patients who have been fasting, can fluctuate between 1 and 6, but in patients who have not fasted it is more frequently between 3 and 5 than 1 to 2.

It was therefore obvious to increase the solubility of pimobendan by the simultaneous administration of an acid. In vitro tests showed, however, that pimobendan in 0.1 N hydrochloric acid (pH value 1.1) dissolved in a quantity of only 100 mg/l (corresponding to a 0.01% solution). In a fumaric acid solution, pH 2.27, only 50 mg/l dissolve (corresponding to a 0.005% solution), in a 20% (by weight) tartaric acid solution, pH 1.2, 960 mg/l dissolve (corresponding to a 0.096% solution), and in a 40% tartaric acid solution, pH 0.7, only 3.9 g/l dissolve (corresponding to a 0.39% solution). None of these levels is sufficient, or the addition of acid required is no longer practicable for dissolving a sufficient quantity of the active substance and thereby ensuring reliable resorption, even if such quantities of these acids are administered orally simultaneously with the active substance.

Surprisingly, the applicants have now succeeded in overcoming the low solubility and high pH dependency of the solubility of pimobendan and ensuring a very satisfactory and more constant resorption, even if there are considerable pH fluctuations in the gastrointestinal tract, by intimately mixing the pimobendan with citric acid in a ratio by weight of at least or less than 1:5 and subsequently processing it with conventional excipients to form a powder, pellets or granules for oral administration. The granules, powder or pellets may also be compressed with suitable excipients to form tablets which may, if desired, also be covered with a flavor-masking coating.

Citric acid is a safe and well tolerated excipient which increases the solubility of pimobendan by a factor of 100, compared with artificial gastric juice (pH 1.2). Thus, 7.6 g/l will dissolve in an aqueous solution of pH 1.4 containing 20% by weight of citric acid, whilst in an aqueous solution of pH 1.0 containing 40% by weight of citric acid as much as 12.1 g of pimobendan will dissolve per liter. However, these quantities of dissolved pimobendan are sufficient to ensure adequate resorption of the active substance even in patients who, when given conventional pimobendan preparations by oral route, showed no blood levels or very low and sharply fluctuating blood levels of pimobendan.

Citric acid is difficult to process into solid preparations. To avoid the formation of salts of pimobendan with citric acid, which would increase the hygroscopicity of the formulation, it is at first sight obvious to process the active substance and acid in two separate granulates. However, it has been found (see Examples 1b to 1d and 2a) that when separated in this way the citric acid cannot fully develop its solubilizing activity. However, it has been found that by intimately mixing pimobendan with citric acid to form a powder mixture which is subsequently processed into granules, a pellet or tablets, it is possible to obtain preparations with small amounts of citric acid which ensure adequate dissolution and sufficiently high blood levels. Technically, this can be achieved for example by nonaqueous granulation, e.g. by granulation with alcohol or by the use of suitable granulating methods which make it possible to add the granulating liquid in accurately metered amounts, with simultaneous drying. Another possibility is the preparation of granules by dry granulation, these granules containing the active substance and citric acid intimately mixed. Owing to the hygroscopic properties of the citric acid, care must be taken to ensure that the preparation forms disintegrate rapidly in the release medium; in the case of tablets, this is achieved by the addition of disintegrants, e.g. Amberlite IRP 88 (methacrylic resin with exchangeable protons), Crospovidone (crosslinked polyvinylpyrrolidone) and microcrystalline cellulose, which will simultaneously improve the poor compression properties of citric acid.

A weight ratio of pimobendan to citric acid of between 1:10 and 1:20 is preferred. The upper limit is defined by the ability of the preparations to be swallowed.

The prevention of sharply fluctuating blood levels (both inter- and intra-individually) by the addition of citric acid can be explained as follows: when the intimate mixture of active substance and citric acid comes into contact with gastric juice, an acidic microsphere is formed around the particles owing to the high rate of dissolution of the citric acid. This microsphere is always acidic, irrespective of the pH of the gastrointestinal juices, and ensures that the finely divided active substance will reliably dissolve and therefore be freely available for resorption.

BRIEF DESCRIPTION OF THE DRAWINGS

FIG. 3 also shows the change in the plasma pimobendan concentration after oral administration to humans of a capsule containing 5 mg. pimobendan and 207 mg of citric acid.

FIG. 4 also shows the change in the plasma pimobendan concentration after oral administration to humans of a capsule containing 2.5 mg. pimobendan and 209 mg of citric acid.

DETAILED DESCRIPTION OF THE PREFERRED EMBODIMENT

Solubility tests have shown, for pH values between 1 and 6, that the active substance dissolves out of this intimate mixture virtually irrespective of the pH. In addition, the active substance also forms supersaturated solutions with the citric acid which remain stable for hours. This ensures a high level of resorption in any case, even in patients with abnormally high pH levels in their gastrointestinal juices. Of the many acids tested for this purpose, citric acid has unexpectedly proved outstanding; apart from acting as an acid, it serves as a solubilizing agent and also as a stabilizer for the active substance solution obtained. An important prerequisite for the dissolving of the active substance independently of the local physiological pH value is the intimate mixing of the pimobendan with the citric acid. For this, it is necessary that both substances be present in powder form or as very small crystals, so that they will make contact with each other over a large surface area.

Figure 1:
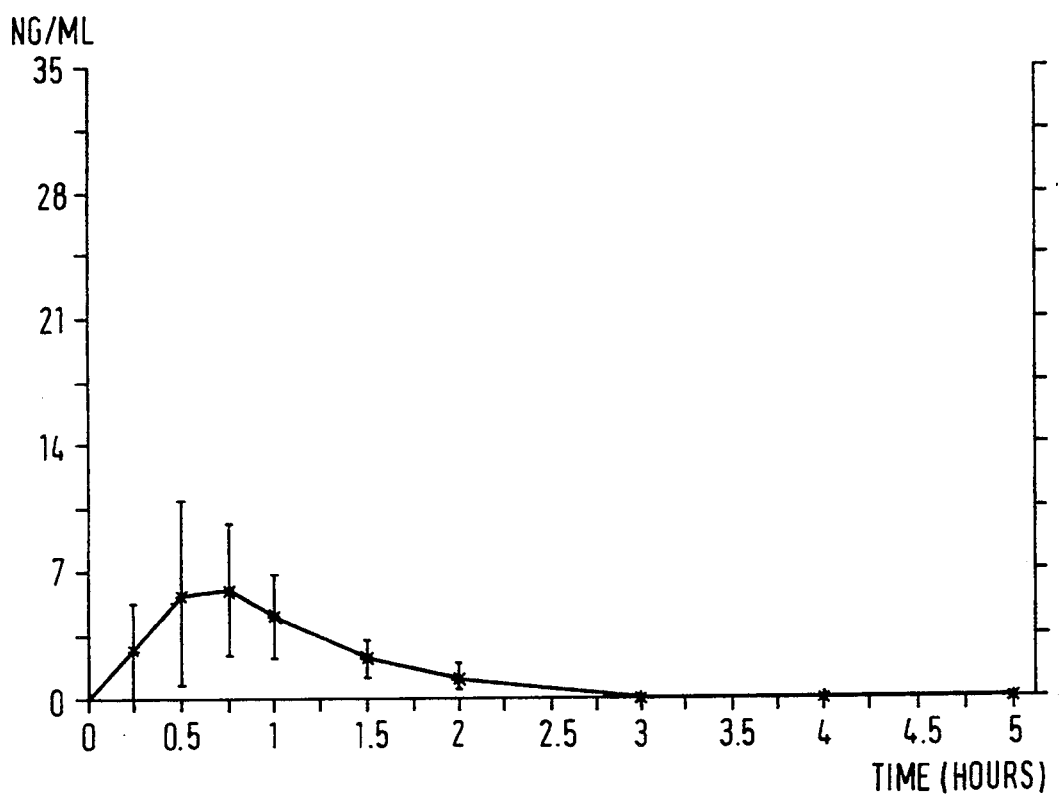
FIG. 1 shows the change in the plasma pimobendan concentration after oral administration to dogs of a tablet containing 5 mg pimobendan without citric acid.
Figure 2:
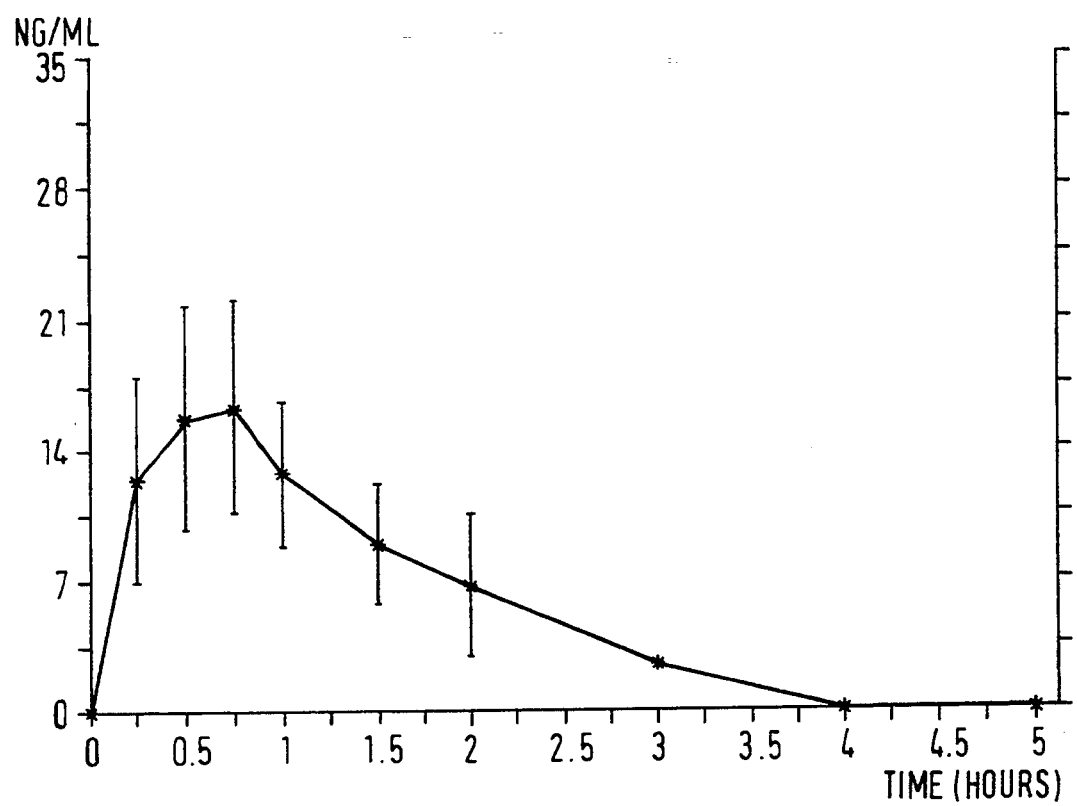
FIG. 2 shows the change in the plasma pimobendan concentration after oral administration to dogs of a tablet containing 5 mg. pimobendan and 50 mg of citric acid.

Tests on dogs after oral administration of a form according to Example 1a containing 5 mg of pimobendan, by comparison with a form according to Example 1b containing 5 mg of pimobendan and 50 mg of citric acid, showed that the pimobendan plasma level was approximately trebled by the form containing the citric acid compared with the form containing no citric acid. The tests were each carried out on 5 experimental animals. The mean curve values found are shown in FIGS. 1 and 2. The plasma level values are shown in nanograms per milliliter as a function of time.

Figure 3:
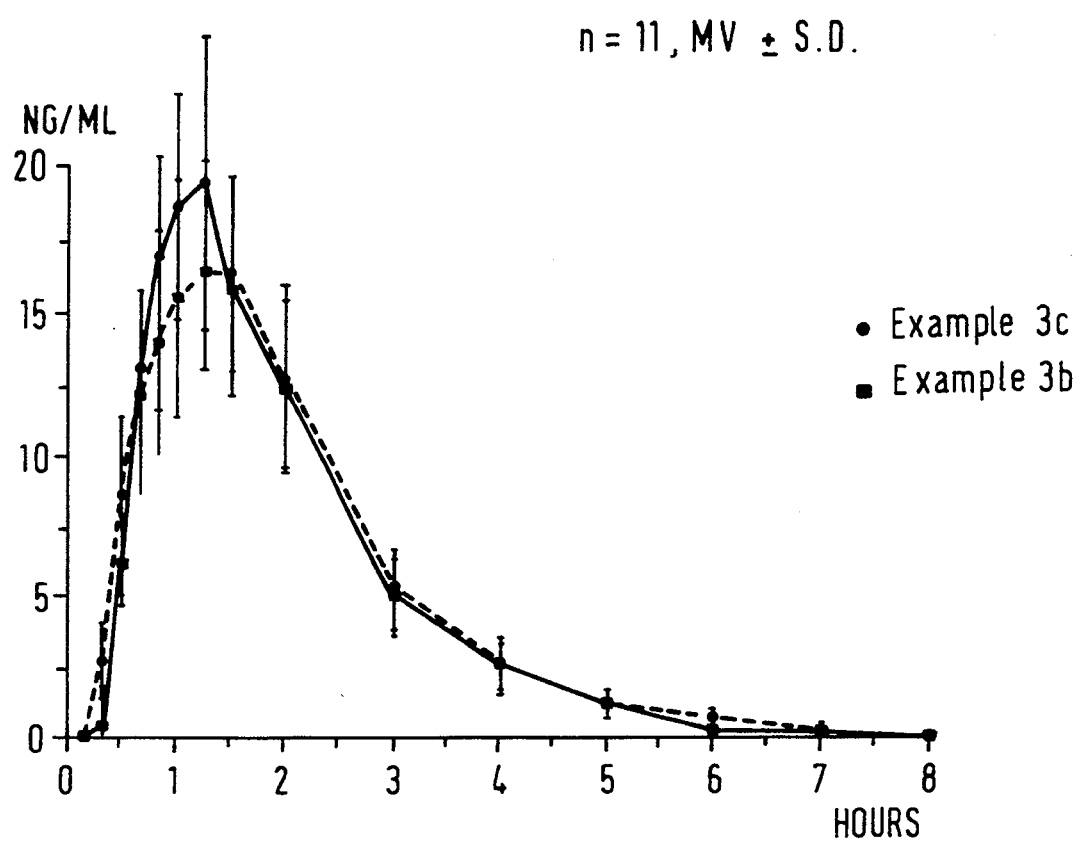
FIG. 3 shows the change in the plasma pimobendan concentration after oral administration to humans of a capsule containing 5 mg. pimobendan and 230 mg of citric acid.
Figure 4:
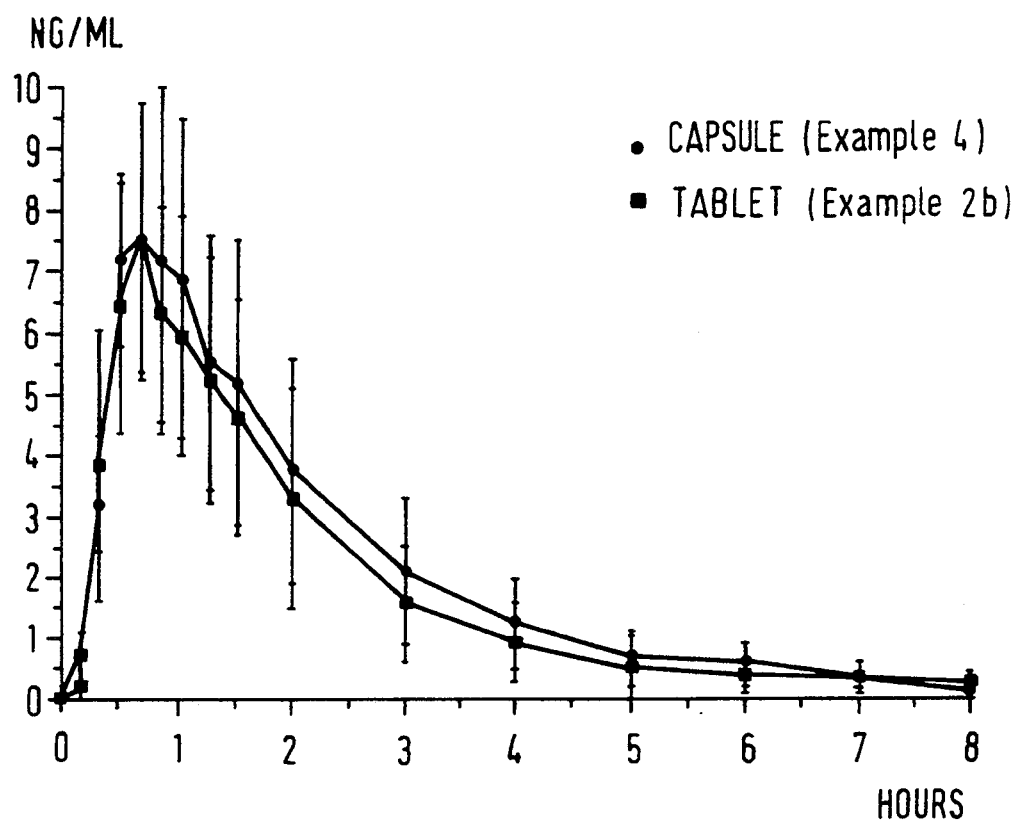
FIG. 4 shows the change in the plasma pimobendan concentration after oral administration to humans of a tablet containing 2.5 mg. pimobendan and 50 mg of citric acid.

Human trials using oral pimobendan forms according to Examples 3b and 3c (capsules) on 11 test subjects gave the mean curves for the plasma levels shown in FIG. 3. The maxima occurred at 1 to 1.5 hours after administration. In addition to the capsule formulations according to Examples 3b and 3c, the plasma level curves of the tablet form according to Example 2b and the capsule form according to Example 4 were each tested on 11 test subjects. It was found that the tablet containing only 50 mg of citric acid according to Example 2b is bioequivalent to the capsule formulation containing 209 mg of citric acid according to Example 4. The plasma levels were obtained by high pressure liquid chromatographic methods, resulting in the mean curves for the plasma levels shown in FIG. 4 (mean values ±standard deviations).

Figure 5:
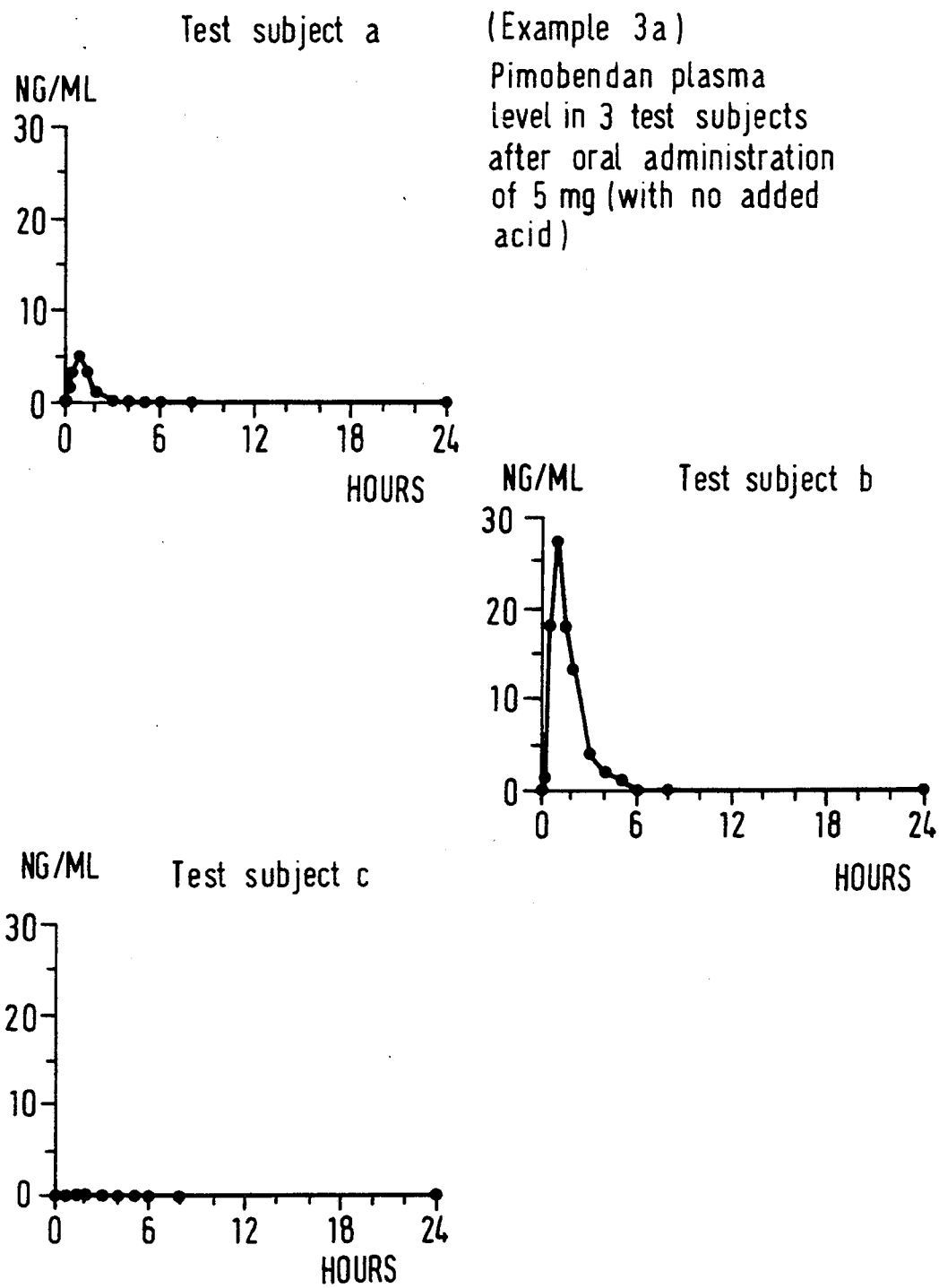
FIG. 5a shows the change in the plasma pimobendan concentration after oral administration to human test subject a of a tablet containing 5 mg. pimobendan without citric acid.
FIG. 5b shows the change in the plasma pimobendan concentration after oral administration to human test subject b of a tablet containing 5 mg. pimobendan without citric acid.
FIG. 5c shows the change in the plasma pimobendan concentration after oral administration to human test subject c of a tablet containing 5 mg. pimobendan without citric acid.

By way of a comparison, a tablet formulation according to Example 3a was administered orally, i.e. a formulation with no citric acid. This resulted in the curves for the plasma levels shown in FIGS. 5a to c on three test subjects. If FIGS. 5a to c are compared with FIG. 4, the superiority of the citric acid preparation, which is made apparent by the reduced fluctuations in plasma levels, over a preparation without citric acid becomes very clear.

It goes without saying, that instead of using pimobendan, one of its possible enantiomers can also be used with equal success.

As a further illustration, by way of example, of the object of this invention, reference is made to the following Examples of oral preparations. In these Examples:

| | |
|---|---|
| Amberlite IRP 88 = | methacrylic resin with exchangeable $H^+$ |
| Collidone 25 = | polyvinylpyrrolidone, average molecular weight 29,000 |
| Avicel = | microcrystalline cellulose |
| Polyplasdone XL = | crosslinked polyvinylpyrrolidone = polyvinylpolypyrrolidone |
| Compritol 888 = | glyceryl monobehenate |
| Tween 80 = | polyoxyethylene-(20)-sorbitan monooleate |
| Explotab = | sodium carboxymethyl starch |
| Aerosil 130 V = | highly dispersed, X-ray amorphous silicon dioxide. |

EXAMPLE 1

Tablets Containing 5Mg of Pimobendan a) Tablets without citric acid
Composition
1 tablet contains (mg)

| | |
|---|---|
| (1) Pimobendan | 5.0 |
| (2) Microcrystalline cellulose | 58.0 |
| (3) Sec. calcium phosphate | 72.0 |
| (4) Corn starch | 54.0 |
| (5) Amberlite IRP 88 | 10.0 |
| (6) Magnesium stearate | 1.0 |
| | 200.0 |

Preparation

Some of the corn starch is dissolved in water with heating and the mixture of ingredients (1) to (4) is granulated therewith. (5) and (6) are added to the dried granules. Tablets 8 mm in diameter and weighing 200 mg are compressed from the finished mixture.

Measurement of rate of dissolution:
According to USP XXIII, paddle method, 150 rpm, in McIlvaine buffer, pH 5.5.
$\bar{x}$ from 3 individual measurements in each case.
Results
After 5 min.: 8.5%
10 min.: 10.2%
15 min.: 10.7%
20 min.: 10.8% 30 min.: 10.8% pimobendan dissolved.

b) Tablets containing 50 mg of citric acid
Composition
1 tablet contains (mg)

| (1) Pimobendan | 5.0 |
| --- | --- |
| (2) Citric acid | 50.0 |
| (3) Microcrystalline cellulose | 42.0 |
| (4) Collidone 25 | 0.5 |
| (5) Sec. calcium phosphate | 52.0 |
| (6) Corn starch | 39.5 |
| (7) Amberlite IRP 88 | 10.0 |
| (8) Magnesium stearate | 1.0 |
| | 200.0 |

Preparation

Some of the corn starch is dissolved in water with heating and ingredient (1), some of (3), (5) and some of (6) are granulated therewith. (2) and the remainder of (3) and (6) are granulated with the aqueous solution of (4). The granules are dried and mixed together. (7) and (8) are added to the mixture of dried granules to form the final mixture. This is then compressed to form tablets 8 mm in diameter and weighing 200 mg.

Note

Active substance and acid are presented in separate granules for ease of manufacture but are mixed together.

Measurement of rate of dissolution: as in Example 1a.
Results
After 5 min.: 7.7%
10 min.: 19.2%
15 min.: 34 %
20 min.: 40.6%
30 min.: 43% pimobendan dissolved.

c) Tablets containing 103 mg of citric acid
Composition
1 tablet contains (mg)

| (1) Pimobendan | 5.0 |
| --- | --- |
| (2) Citric acid | 103.0 |
| (3) Microcrystalline cellulose | 35.0 |
| (4) Collidone 25 | 1.0 |
| (5) Sec. calcium phosphate | 31.5 |
| (6) Corn starch | 81.5 |
| (7) Amberlite IRP 88 | 10.0 |
| (8) Magnesium stearate | 3.0 |
| | 270.0 |

Preparation
Analogous to Example 1b.
Tablets: 9 mm diameter, 270 mg in weight.
Note
The active substance and acid are present in separate granulates for ease of manufacture but are mixed together.

d) Tablets containing 206 mg of citric acid
Composition
1 tablet contains (mg)

| (1) Pimobendan | 5.0 |
| --- | --- |
| (2) Citric acid | 206.0 |
| (3) Avicel | 50.0 |
| (4) Collidone 25 | 2.0 |
| (5) Sec. calcium phosphate | 63.0 |
| (6) Corn starch | 46.0 |
| (7) Amberlite IRP 88 | 20.0 |
| (8) Magnesium stearate | 3.0 |
| | 395.0 |

Preparation
Analogous to Example 1b.
Tablets: 11 mm in diameter, weight 395 mg.
Note
The active substance and acid are present in separate granulates for ease of manufacture but are mixed together.
Measurement of rate of dissolution: analogous to Example 1a.
Result
After 5 min.: 23.8%
10 min.: 59%
15 min.: 67%
30 min.: 69% pimobendan dissolved.

EXAMPLE 2

Tablets Containing 2.5 Mg of Pimobendan a) Tablets containing 103 mg of citric acid
Composition
1 tablet contains (mg)

| (1) Pimobendan | 2.5 |
| --- | --- |
| (2) Corn starch | 23.0 |
| (3) Microcrystalline cellulose | 26.0 |
| (4) Anhydrous calcium phosphate | 31.5 |
| (5) Polyplasdone XL | 59.0 |
| (6) Citric acid, fine particles (anhydrous) | 103.0 |
| (7) Compritol 888 | 5.0 |
| | 250.0 |

Preparation
(1) to (4) are granulated with aqueous starch solution. The other tablet ingredients are added to the dry granules to make the final mixture. From this, tablets are compressed measuring 9 mm in diameter and weighing 250 mg.
Note
The active substance and acid occur separately, for ease of manufacture, but are subsequently mixed together.
Measurement of speed of dissolution: analogous to Example 1a.
Results
After 5 min.: 18.7%
10 min.: 20.5%
20 min.: 21.8%
30 min.: 22.2%
60 min.: 22.7% pimobendan dissolved.

b) Tablets containing 50 mg of citric acid
Composition
1 tablet contains (mg)

| (1) Pimobendan | 2.5 |
| --- | --- |
| (2) Anhydrous powdered citric acid | 50.0 |
| (3) Avicel PH 101 | 13.0 |
| (4) Anhydrous calcium hydrogen phosphate | 15.0 |
| (5) Undried corn starch | 6.0 |
| (6) Collidone 25 | 0.5 |

| | |
|---|---|
| (7) Insoluble polyvinylpyrrolidone | 59.0 |
| (8) Compritol 888 | 3.0 |
| (9) Magnesium stearate | 1.0 |
| | 150.0 |

Preparation (6) is dissolved in ethanol and the mixture of ingredients (1) to (5) is granulated therewith. (7) to (9) are added to the dry granules to form the mixture ready for compression. This mixture is compressed to form tablets measuring 8 mm in diameter.

Note

Active substance and acid are present together in the same granulate.

Measurement of rate of dissolution: analogous to Example 1a.

Result

After 15 min.: 71.1%

30 min.: 85% pimobendan dissolved.

EXAMPLE 3

Capsules Containing 5 Mg of Pimobendan a) Capsules without citric acid

Composition 1 capsule contains (mg)

| | |
|---|---|
| Pimobendan | 5.0 |
| Lactose | 90.25 |
| Corn starch | 36.0 |
| Tween 80 | 0.5 |
| Explotab | 8.0 |
| Magnesium stearate | 0.25 |
| | 140.0 |

Preparation

The individual powders are intensively mixed together and packed into size 4 hard gelatin capsules (140 mg per capsule).

b) Capsules containing 230 mg of citric acid

Composition 1 capsule contains (mg)

| | |
|---|---|
| (1) Pimobendan | 5.0 |
| (2) Citric acid | 230.45 |
| (3) Collidone 25 | 3.78 |
| (4) Magnesium stearate | 0.77 |
| | 240.00 mg |

Preparation (1) and (2) are intensively mixed together and granulated with an alcoholic solution of (3). (4) is added to the dried granulate. The final mixture thus obtained is packed into size 1 hard gelatin capsules (240 mg per capsule).

Note

Active substance and acid are present together in one and the same granulate.

Measurement of rate of dissolution: analogous to Example 1a.

Result

After 5 min: 100% pimobendan dissolved.

c) Capsules containing 207 mg of citric acid composition:

1 capsule contains (mg)

| | |
|---|---|
| (1) Pimobendan, finely ground | 5.0 |
| (2) Citric acid | 206.5 |
| (3) Microcrystalline cellulose | 40.0 |
| (4) Aerosil 130 V | 11.0 |
| (5) Collidone 25 | 4.0 |
| (6) Magnesium stearate | 1.5 |
| | 268.0 |

Preparation (1) is triturated with (2). (3) and (4) are added to the triturated material. The mixture is granulated with an alcoholic solution of (5). (6) is mixed into the dry granulate. The finished mixture is packed into size 1 capsules (268 mg per capsule).

Note

Active substance and acid are present in one and the same granulate.

Measurement of rate of dissolution: analogous to Example 1a.

Result

After 5 min.: 84.1%

10 min.: 90.2%

15 min.: 91.7%

30 min.: 92.5% pimobendan dissolved.

EXAMPLE 4

Capsules Containing 2.5 Mg of Pimobendan

Capsules Containing 209 Mg of Citric Acid

Composition 1 capsule contains (mg)

| | |
|---|---|
| (1) Pimobendan | 2.5 |
| (2) Powdered citric acid | 209.0 |
| (3) Microcrystalline cellulose | 40.0 |
| (4) Silicon dioxide | 11.0 |
| (5) Polyvinylpyrrolidone | 4.0 |
| (6) Magnesium stearate | 1.5 |
| | 268.0 |

Preparation

Analogous to Example 3c.

Note

Active substance and acid are present in one and the same granulate.

Measurement of rate of dissolution: analogous to Example 1a.

Result

After 15 min.: 96.5%

30 min.: 99.1% pimobendan dissolved.

EXAMPLE 5

Film Coated Tablet Containing 2.5 Mg of Pimobendan

Tablets Containing 50 Mg of Citric Acid

Composition 1 tablet contains (mg)

| | |
|---|---|
| (1) Pimobendan | 2.5 |
| (2) Powdered anhydrous citric acid | 50.0 |
| (3) Avicel PH 101 | 13.0 |
| (4) Anhydrous calcium hydrogen phosphate | 15.0 |
| (5) Undried corn starch | 6.0 |
| (6) Collidone 25 | 0.5 |
| (7) Insoluble polyvinylpyrrolidone | 59.0 |
| (8) Compritol 888 | 3.0 |
| (9) Magnesium stearate | 1.0 |

-continued

| |
|---|
| 150.0 |

Preparation

The preparation is as described in Example 2b, but the finished mixture is compressed into biconvex tablets. These are coated with 5 mg of hydroxypropylmethylcellulose per tablet.

Note

Active substance and acid are together in the same granulate.

Measurement of rate of dissolution: analogous to Example 1a.

Results

After 10 min.: 76.8%

30 min.: 86.1% pimobendan dissolved.

What is claimed is:

1. A pharmaceutical composition of matter consisting essentially of an intimate dry admixture of a therapeutically effective amount of powdered pimobendan and powdered citric acid wherein said admixture is up to about one pad by weight of pimobendan per no less than about five pads by weight of citric acid and a pharmaceutically acceptable carder, said composition being filled into capsules for oral administration.

2. The pharmaceutical composition of matter as recited in claim 1 wherein said admixture is up to about one pad by weight of pimobendan per about ten parts by weight of citric acid.

3. The pharmaceutical composition of matter as recited in claim 1 wherein said admixture is up to about one pad by weight of pimobendan per about twenty parts by weight of citric acid.

4. The pharmaceutical composition of matter as recited in claim 3 wherein said admixture is up to about one part by weight of pimobendan per about twenty to about ten parts be weight of citric acid.

5. A pharmaceutical composition of matter consisting essentially of an intimate dry admixture of powdered pimobendan and powdered citric acid wherein said admixture is up to about one part be weight of pimobendan per no less than about five parts by weight of citric, a pharmaceutically acceptable carder and a dis-integrant, compressed into tablet form for oral administration.

6. The pharmaceutical compositions of matter as recited in claim 4 wherein the tablet is coated with a flavor-masking component.

7. The pharmaceutical composition of matter as recited in claim 4 wherein said admixture is up to about one part by weight of pimobendan per about ten parts by weight of citric acid.

8. The pharmaceutical composition of matter as recited in claim 5 wherein said admixture is up to about one part by weight of pimobendan per about twenty parts by weight of citric acid.

9. The pharmaceutical composition of matter as recited in claim 4 wherein said admixture is up to about one part by weight of pimobendan per about twenty to about ten parts by weight of citric acid.

* * * * *

UNITED STATES PATENT AND TRADEMARK OFFICE
CERTIFICATE OF CORRECTION

| | |
|---|---|
| PATENT NO. | : 5,364,646 |
| APPLICATION NO. | : 08/033659 |
| DATED | : November 15, 1994 |
| INVENTOR(S) | : Peter Gruber, Willy Roth and Gottfried Schepky |

It is certified that error appears in the above-identified patent and that said Letters Patent is hereby corrected as shown below:

In Column 9, line 24 of Claim 1, change "pad" to --part--.

In Column 9, line 25 of Claim 1, change "pads" to --parts--.

In Column 9, line 26 of Claim 1, change "carder" to --carrier--.

In Column 9, line 31 of Claim 2, change "pad" to --part--.

In Column 10, line 3 of Claim 3, change "pad" to --part--.

In Column 10, line 12 of Claim 5, change "be" to --by--.

In Column 10, line 14 of Claim 5, change "carder" to --carrier--.

Signed and Sealed this

Seventeenth Day of April, 2007

JON W. DUDAS
*Director of the United States Patent and Trademark Office*